(12) United States Patent
Rohrer et al.

(10) Patent No.: US 9,861,587 B2
(45) Date of Patent: Jan. 9, 2018

(54) COMPOSITION AND METHOD FOR TREATING KETOSIS IN COWS

(75) Inventors: James M. Rohrer, Burlington, WI (US); Patrick D. French, North Chesterfield, VA (US); Keith F. Moritz, Fort Atkinson, WI (US)

(73) Assignee: RP FEED COMPONENTS, LLC, East Troy, WI (US)

( * ) Notice: Subject to any disclaimer, the term of this patent is extended or adjusted under 35 U.S.C. 154(b) by 1071 days.

(21) Appl. No.: 13/227,633

(22) Filed: Sep. 8, 2011

(65) Prior Publication Data

US 2013/0064884 A1   Mar. 14, 2013

(51) Int. Cl.
| | |
|---|---|
| *A61K 9/48* | (2006.01) |
| *A61K 31/19* | (2006.01) |
| *A61K 31/198* | (2006.01) |
| *A61K 31/223* | (2006.01) |
| *A61K 31/57* | (2006.01) |
| *A61K 31/7004* | (2006.01) |
| *A61K 33/24* | (2006.01) |
| *A61P 3/00* | (2006.01) |

(52) U.S. Cl.
CPC .......... *A61K 9/4825* (2013.01); *A61K 31/198* (2013.01)

(58) Field of Classification Search
CPC ............................ A61K 31/198; A61K 9/4825
See application file for complete search history.

(56) References Cited

U.S. PATENT DOCUMENTS 3,709,987 A * 1/1973 Wiilliams ..................... 424/602
5,741,506 A 4/1998 Bauchart et al.

OTHER PUBLICATIONS

Chung, Yi-hua. (Avail. to the public 2003). Thesis: "Effects of free methionine and lysine on in vitro fermentation and in vivo performance and Ruminal fermentation of late lactation holstein cows". [retrieved on Jan. 25, 2012]. Retrieved on the internet <URL: http://etd.lsu.edu/docs/available/etd-0710103-102634/unrestricted/Chung_thesis.pdf>).*
J.C. Shaw, "Studies on Ketosis in Dairy Cattle. VII. The Efficacy of B Vitamins and Methionine in the Treatment of Ketosis," J. Dairy Sci., vol. 29, No. 3, pp. 131-139, Mar. 1946.
McCarty et al., "Bovine Ketosis and Depressed Fat Test in Milk: A Problem of Methionine Metabolism and Serum Lipoprotein Aberration," J. Dairy Sci., vol. 51, No. 2, pp. 459-462, 1968.
Waterman et al., "Methionine Hydroxy Analog Treatment of Bovine Ketosis: Effects on Circulating Metabolites and Interrelationships," J. Dairy Sci., vol. 55, No. 10, pp. 1513-1516, 1972.
Griel et al., "Milk Production Response to Feeding Methionine Hydroxy Analog to Lactating Dairy Cows," J. Dairy Sci., vol. 51, No. 11, pp. 1866-1868, 1968.
Henricks et al., "Body Condition Scoring as a Tool for Dairy Herd Management," Extension Circular 363, Penn State College of Agriculture, pp. 1-14, 1989.

* cited by examiner

*Primary Examiner* — Anoop Singh
*Assistant Examiner* — Doan Phan
(74) *Attorney, Agent, or Firm* — Oliff PLC

(57) ABSTRACT

A method for prophylactic treatment of ketosis in a calving cow, the method including orally administering to the cow within a time period of about 12 hours after calving an effective dose of from 20 to 30 g of rumen protected methionine. If the cow falls into a risk category, the cow is administered the dose of rumen protected methionine once a day on the second, third, fourth, and fifth days after calving. Also, a composition including a gelatin capsule and rumen-protected methionine contained within the gelatin capsule that may be administered to a calving cow for the prophylactic treatment of ketosis. The composition may further contain within the gelatin capsule one or more other compounds known to have efficacy on fat or glucose metabolism, such as glucose, propylene glycol, niacin, choline, chromium, calcium propionate, and glucocorticoids.

12 Claims, No Drawings

COMPOSITION AND METHOD FOR TREATING KETOSIS IN COWS

BACKGROUND

This disclosure is generally directed to a composition and a method for the prophylactic treatment of ketosis and related calving disorders in calving cows.

When lactation starts in dairy cows, the onset of milk production is sudden, and the nutritional requirements of the lactating cow become very high. Lactogenesis increases the demand for glucose as a precursor for lactose synthesis. Unlike monogastric mammals, ruminants—such as dairy cows—rely heavily on gluconeogenesis in the liver to meet their glucose requirements, because less glucose is absorbed in the lower digestive tract. Thus, during lactation, increased supply and digestion of carbohydrates in the rumen is necessary to meet the energy requirements of the cow. As parturition approaches, the blood sugar level of cows continues to decrease and, after parturition, it further decreases sharply.

Substantial metabolic adjustment is required to provide substrates for milk synthesis after calving. Energy deficit in early lactation is prevalent. Feed intake is depressed around calving and thus the amount of available propionate, the major glucogenic precursor formed in the rumen, is usually insufficient. When the energy requirement of the cow exceeds its energy intake, the metabolism of the cow adjusts to meet the deficit from body reserves, such as fatty tissues. Long-chain fatty acids (or non-esterified fatty acids, NEFAs) are mobilized from body fat. NEFAs, already elevated from around seven days prepartum, are a significant source of energy to the cow during the early postpartum period, and the greater the energy deficit the higher the concentration of NEFA in the blood. The circulating NEFAs are taken up by the liver and are oxidized to carbon dioxide or ketone bodies (e.g. 3-hydroxybutyrate, acetoacetic acid, and acetone), or are reconverted by esterification into triglycerides and stored. Meanwhile, the capacity of the liver for synthesizing very low density lipoproteins to export triglycerides from the liver is limited.

When the amount of ketone bodies formed exceeds the amount of ketone bodies metabolized by the cow, the ketone bodies accumulate in the blood and in the urine, which are conditions respectively known as ketonemia and ketonuria. These conditions fall under the broader classification of ketosis. Dairy cows suffering from ketosis exhibit symptoms such as poor appetite, decreased body weight, and lower milk production. Because acetoacetic acid and 3-hydroxybutyric acid are strong acids, excessive concentrations of these ketone bodies in the blood can exceed the buffering capacity of the cow's body, which in turn lowers the pH of the blood and can lead to a fatal state called ketoacidosis. Because ruminants produce butyric acid as a fermentation product in the digestive tract, which is a precursor to 3-hydroxybutyric acid, the concentration of ketone bodies in the blood even at a physiological state is higher than in non-ruminants and, therefore, the incidence of ketosis in ruminants is high.

Ketosis may be treated by intravenous administration of a solution of a sugar, such as glucose, xylitol, or the like, but the effect on reduction of the concentration of ketone bodies is transitory and lasts only a short period of time. Although continuous intravenous injection over an extended time period would address this problem in theory, such a solution is not practical in dairy farming. Another option is to repeat such single administrations frequently, which, again, is not very practical.

Other treatment options include injections of hormones or steroids, administration of glucose precursors such as propylene glycol and sodium propionate, and supplementation of other nutrients known to increase blood sugar and thus reduce ketones and fat mobilization.

For prevention of ketosis of cows, studies have indicated several strategies, including pre-fresh nutritional management combined with preventing obesity in dry cows, maximizing energy intake in early lactation, avoid feeding large quantities of poor quality grass silage high in butyric acid during the ketosis susceptible period, and supplementing the diet with glucose precursors such as propylene glycol and sodium propionate.

Some studies have evaluated the effect of various forms of methionine in the treatment or prevention of ketosis in dairy cows. Shaw, J. C., "Studies on Ketosis in Dairy Cattle. VII. The Efficacy of B Vitamins and Methionine in the Treatment of Ketosis," J. Dairy Sci., 29:131 (1946) reports the unsuccessful treatment of two ketotic cows using daily injections or oral administration of 12.5 g of DL-methionine. McCarty et al., "Bovine Ketosis and Depressed Fat Test in Milk: A Problem of Methionine Metabolism and Serum Lipoprotein Aberration," J. Dairy Sci., 51:459-462 (1968) reports that the oral administration of the methionine hydroxy analog (MHA) (DL-$\alpha$-hydroxy-$\gamma$-methylmercaptobutyrate calcium) aided in alleviating symptoms of bovine ketosis. Waterman et al., "Methionine Hydroxy Analog Treatment of Bovine Ketosis: Effects on Circulating Metabolites and Interrelationships," J. Dairy Sci., 55:1513-1516 (1972) reports on a trial where six cases of clinical ketosis were treated with MHA orally in 40 g doses once daily for seven days. The data demonstrated that serum ketone levels fell slowly over a 21-day examination period, but never returned to normal levels. Waterman concludes that because spontaneous recovery from ketosis is an accepted phenomenon, and in view of other studies, treating ketosis with MHA was of questionable benefit.

Griel et al., "Milk Production Response to Feeding Methionine Hydroxy Analog to Lactating Dairy Cows," J. Dairy Sci., 51:1866-1868 (1968) evaluated the effectiveness of MHA in preventing ketosis. In that trial, MHA was supplemented into the feed as a top dressing in an amount to supply 40 g and 80 g daily to two respective test groups of cows. A third group of cows, the control group, were not fed any MHA. Feeding of the MHA began three weeks preparturition and continued for eight weeks thereafter. Because none of the animals, including those in the control group, showed clinical signs of ketosis during the trial, the results were inconclusive.

Example 2 of U.S. Pat. No. 5,741,506 to Bauchart et al. evaluated the extent to which rumen protected methionine could limit ketosis in fatty cows receiving rations with low energy concentrations. At three to four weeks preparturition, the cows were fed 40 g/day protected methionine (about 28 g digestible methionine) in a bucket with 200 g of untanned cake for five days. Then, at the third or fifth day following parturition, the same feeding was done daily up to the sixth week of lactation. The data, as summarized in Table 8, demonstrates a reduction of ketone bodies in the serum at week 2 of lactation, which then significantly increased at week four of lactation.

SUMMARY

Disclosed herein is a method for prophylactic treatment of ketosis in a calving cow, the method comprising orally administering to the cow within a time period of about 24 hours after calving an effective dose of from 20 to 30 g of rumen protected bioavailable methionine. If the cow falls into a risk category, the cow is administered the dose of rumen protected methionine once a day on the second, third, fourth, and fifth days after calving.

Also disclosed is a composition comprising a gelatin capsule and rumen-protected methionine contained within the gelatin capsule that may be administered to a calving cow for the prophylactic treatment of ketosis. The composition may further contain within the gelatin capsule one or more other compounds known to have efficacy on fat or glucose metabolism, such as glucose, propylene glycol, niacin, choline, chromium, calcium propionate, and glucocortieoids.

DETAILED DESCRIPTION OF EMBODIMENTS

Embodiments herein relate to administering a dosage of rumen protected methionine to cows within a certain period of time immediately after calving for the prophylactic treatment of ketosis and related calving disorders.

As used herein, the term "prophylactic" encompasses "preventing," "inhibiting," and "ameliorating" as defined herein. It will be understood by those skilled in the art that it is not always possible to distinguish between "preventing," "inhibiting," and "ameliorating" because the ultimate inductive event or events may be unknown, latent, or the afflicted animal is not ascertained until well after the occurrence of the event or events.

As used herein, "preventing" refers to a result of treatment where an animal may be predisposed to the disease, condition, or disorder but does not yet experience or display the pathology or symptomatology of the disease, condition, or disorder.

As used herein, "inhibiting" refers to a result of treatment that delays the onset of the pathology and/or symptomatology of a disease, condition, or disorder; or slows the progression of the pathology and/or symptomatology of the disease, condition, or disorder; or arrests further development of the pathology and/or symptomatology of the disease, condition, or disorder in an animal already experiencing or displaying the pathology or symptomatology of the disease, condition, or disorder.

As used herein, "ameliorating" refers to a result of treatment that reverses or reduces at least in part the pathology and/or symptomatology of a disease, condition, or disorder in an animal already experiencing or displaying the pathology or symptomatology of the disease, condition, or disorder.

As used herein, "ketosis" refers to both complicated and uncomplicated ketosis, where complicated ketosis is a condition that is accompanied by additional health disorder whereas uncomplicated ketosis is a condition that is not accompanied by other health disorders.

As used herein, "related calving disorders" refers to, for example, ketosis, fatty liver, metritis, and negative energy balance.

Ruminant animals have a stomach divided into four morphologically distinct compartments: the rumen, the reticulum, the omasum, and the abomasum. The rumen and the reticulum are derived from the terminal portion of the esophagus, and only the omasum and the abomasum are considered to be a genuine stomach. Bacteria present in the rumen enable ruminants to digest cellulosic materials such as grass. Conventional digestion occurs in the abomasum, sometimes called the "true stomach." Well-known ruminants include cattle, sheep, and goats.

The rumen, which is essentially a continuous fermenter, supports a variety of microorganisms under near neutral pH conditions that attack and digest much of the ingested feedstuffs consumed by a ruminant as part of its normal life cycle. Ingested protein material is broken down in the rumen to soluble peptides and amino acids that are used as nutrients by the microorganisms. A stream of ingesta, rich in microbial cells, passes out of the rumen into the omasum. The function of the omasum is to separate liquids and solids. Much of the liquid reenters the rumen while the remainder of the material enters the abomasum. Digestion and absorption then proceed in the abomasum in a manner similar to that found in monogastrics. Enzymes secreted into the lumen of the abomasum digest much of the material, including the microbial cells. The digested microbial cells provide protein and amino acids to the ruminant.

The microbial action of the rumen has the great advantage of being able to convert many feed components which have no direct nutritive value for the host into products which can be assimilated and utilized by the host. For example, urea may be converted to microbial protein which subsequently may be digested and utilized by the host animal. Cellulose may be converted to a mixture of volatile fatty acids which can serve as a source of energy to the host.

Unfortunately, this microbial action also presents certain disadvantages. For instance, soluble proteins of high nutritive value may be broken down and digested in the rumen and in part resynthesized into microbial protein of lower nutritive value. Amino acids are also chemically changed by the rumen microorganisms, which convert amino acids to carbon dioxide, volatile fatty acids, and ammonia. Thus, when physiologically active amino acids, such as methionine, are orally fed to a cow, a substantial part is decomposed by microorganisms in the rumen, making it difficult or impossible for the animal to effectively utilize all of the administered amino acids. Thus, it is important to pass the biologically active substances through the rumen without decomposition by microorganisms to allow the biologically active substances to be effectively digested and absorbed in the abomasum and subsequent digestive tract.

There are a number of methodologies that are designed to increase the amount of a nutrient that passes through the rumen without being degraded by the rumen microflora, thereby delivering a larger portion of that nutrient to the lower gastrointestinal tract, including: heat and chemical treatment, encapsulation and coating, use of amino acid analogs, and polymeric compounds of amino acids. For instance, it has been proposed to coat ruminant animal feed additives containing biologically active substances with protective substances, such as fatty acids, hardened animal oils, and hardened vegetable oils. Another method proposed utilizes the difference in pH between the rumen and the abomasum by coating with a polymer that is insoluble in the environment of the rumen but is soluble in the strongly acidic abomasum. Such polymers include polyvinylpyrrolidone, polyamides, and celluloses that have been chemically modified.

As used herein, "rumen protected methionine" refers to methionine, a salt of methionine, or analogs thereof that is coated or encapsulated in such a way that protects the methionine from degradation in the rumen, allowing the methionine to bypass the rumen and be digested and absorbed in the abomasum and subsequent digestive tract.

The rumen protected methionine may be characterized by its bioavailability rate. "Bioavailability rate" refers to the weight percentage of the initial amount of methionine administered to the cow that is delivered past the rumen and then absorbed into the blood stream through the abomasum and subsequent digestive tract. This is the composition's rumen bypass rate, which is the weight percentage of the methionine contained in the composition before entering the rumen that remains in the composition upon exiting the rumen multiplied by the intestinal digestibility rate, which is the weight percentage of the methionine passed from the rumen that is digested and absorbed in the abomasum and subsequent digestive tract.

The higher the bioavailability of the composition, the less of the composition that needs to be administered to the cow to administer an effective amount of methionine to the cow. The term "effective amount" means an amount of methionine that needs to be absorbed into the cow's bloodstream for the prophylactic treatment of the disease, disorder, or condition being treated. This may vary depending on the cow, the disease, disorder, or condition being treated, and other factors.

Exemplary forms of methionine that may be rumen protected include D,L-methionine, t-butyl ester of methionine, D,L-2-hydroxy-4-(methylthio)-butanoic acid (HMB) more commonly known as Methydroxy analog (MHA), and isopropyl ester of the D,L-2-hydroxy-4-(methylthio)-butanoic acid (HMBi). An exemplary rumen protected methionine is MEPRON, available from Evonik Corporation. MEPRON is a form of D,L-methionine encapsulated in ethylcellulose that is time-released in the intestine.

To ensure proper dosage, the rumen protected methionine may be administered orally to the cow, as opposed to feeding the rumen protected methionine to the cow, such as by mixing it with or top dressing the cow's feed. For example, the rumen protected methionine may be placed into one or more gelatin capsules, such as the #07 gelatin capsules available from Torpac, Inc. The capsules may then be administered to the cow by hand or with a bolus gun.

An effective amount of methionine for the prophylactic treatment of ketosis in calving cows is from about 20 to about 30 grams of methionine per day, such as from about 20 to 30 grams, or from 20 to about 30 grams, or from 20 to 30 grams, or from 20 to 27 grams, or from 20 to 25 grams, or from 23 to 30 grams, or from about 25 to 30 grams of methionine per day. For the highest levels of efficacy, an effective amount of the rumen protected methionine should be administered to the cow as soon after calving as possible, such as, for example, within 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, or 24 hours after calving, although longer time periods are within the scope of this disclosure.

Administration of this dosage may be repeated daily for a period of, for example, one day, two days, three days, four days, five days, six days, or seven days after calving, although longer time periods are within the scope of this disclosure. However, for most calving cows, a single administration of an effective amount of methionine is sufficient for the prophylactic treatment of ketosis in calving cows, especially in cows that do not fall within a risk category. The risk categories are: a body condition score greater than 4, depressed milk weights, retained placenta, dry period over 60 days long, and/or twins. A "body condition greater than 4" is determined in accordance with Henricks, A. J. and V. A. Isler, "Body-condition Scoring as a Tool for Dairy Herd Management," Extension Circular 363, Penn State College of Agriculture (1989), the disclosure of which in incorporated by reference herein in its entirety. For example, a score of 4 is determined when:

Individual short ribs are distinguishable only by firm palpation;
Short ribs appear flat or rounded, with no overhanging shelf effect;
Ridge formed by backbone in chine region is rounded and smooth;
Loin and rump regions appear flat;
Hooks are rounded and the span between them is flat; and
Area of tail head and pin bones is rounded, with evidence of fat deposit.

As used herein, a cow is determined to have "depressed milk weights" if the cow's milk weight production is greater than one standard deviation less from the mean.

If the cow falls into one or more risk categories, the at-risk cow may be administered additional daily dosages of an effective amount of methionine for a period of, for example, one day, two days, three days, four days, five days, six days, or seven days after calving, although longer time periods are within the scope of this disclosure.

Although it is preferable to administer a daily dosage of an effective amount of methionine in a single administration, the daily dosage may be divided or split up into two or more administrations within the prescribed period, so long as an effective amount of methionine in total is administered within the prescribed period.

The rumen protected methionine may be supplemented with one or more other compounds known to have efficacy on fat or glucose metabolism. Such compounds include glucose, propylene glycol, niacin, choline, chromium, calcium propionate, and glucocorticoids.

EXAMPLE

During two 12-month periods, sample populations of 700 lactating animals were administered 45 grams of MEPRON to each test cow by way of a bolus and balling gun as soon as possible after calving, within 24 hours postpartum. The dosage was repeated up to four days for a cow determined to fall into a risk category. Daily milk production was recorded each day. Non-esterified fatty acids and beta-hydroxybutyrate levels were also randomly measured and recorded pre- and post-fresh. It was also observed that retained placentas decreased from 9% to 3%, and displaced abomasums decreased from 3% to 1%.

What is claimed is:
1. A method for prophylactic treatment of ketosis in a calving cow, the method comprising:
   orally administering to the cow within a time period of about 18 hours after calving an amount of rumen protected methionine that provides an effective dose of methionine of from about 20 to about 30 g; and
   determining whether the cow falls into a risk category selected from the group consisting of:
   a body condition score greater than 4,
   depressed milk weights,
   retained placenta,
   dry period over 60 days long, and
   twins;
   wherein:
   if the cow falls within a risk category, the cow is administered the effective dose of rumen protected methionine once a day on the second, third, fourth, and fifth days after calving.

2. The method of claim 1, wherein the methionine is selected from the group consisting of D,L-methionine, t-butyl ester of methionine, D,L-2-hydroxy-4-(methylthio)-butanoic acid (HMB), and isopropyl ester of D,L-2-hydroxy-4-(methylthio)-butanoic acid (HMBi).

3. The method of claim 2, wherein the rumen protected methionine comprises D,L-methionine encapsulated in ethylcellulose.

4. The method of claim 1, wherein the rumen protected methionine is inside a gelatin capsule, and the gelatin capsule is orally administered to the cow.

5. The method of claim 4, wherein the gelatin capsule is orally administered to the cow with a bolus gun.

6. The method of claim 5, wherein further contained in the gelatin capsule is one or more supplements selected from the group consisting of glucose, propylene glycol, niacin, choline, chromium, calcium propionate, and glucocorticoids.

7. The method of claim 1, wherein the effective dose of methionine is from 20 to 30 g.

8. The method of claim 1, wherein the rumen protected methionine is administered to the cow within a time period of about 12 hours after calving.

9. The method of claim 1, wherein the rumen protected methionine is administered to the cow within a time period of about 6 hours after calving.

10. The method of claim 1, wherein the rumen protected methionine is administered to the cow within a time period of about 1 hour after calving.

11. The method of claim 1, wherein the cow is determined to not fall within a risk category, and the effective dose of rumen protected methionine is administered to the cow only once after calving.

12. A method for prophylactic treatment of a retained placenta and/or a displaced abomasum in a calving cow, the method comprising:
    orally administering to the cow within a time period of about 18 hours after calving an amount of rumen protected methionine that provides an effective dose of methionine of from about 20 to about 30 g; and
    determining whether the cow falls into a risk category selected from the group consisting of:
        a body condition score greater than 4,
        depressed milk weights,
        retained placenta,
        dry period over 60 days long, and
        twins;
    wherein:
        if the cow falls within a risk category, the cow is administered the effective dose of rumen protected methionine once a day on the second, third, fourth, and fifth days after calving.

* * * * *